United States Patent
Waechter-Stehle et al.

(10) Patent No.: US 9,025,840 B2
(45) Date of Patent: May 5, 2015

(54) MOTION VISUALISATION IN ANGIOGRAPHIC IMAGES

(75) Inventors: Irina Waechter-Stehle, Hamburg (DE); Alexandra Groth, Hamburg (DE); Ronaldus Petrus Johannes Hermans, Den Bosch (NL); Matthias Bertram, Aachen (DE)

(73) Assignee: Koninklijke Philips N.V., Eindhoven (NL)

( * ) Notice: Subject to any disclaimer, the term of this patent is extended or adjusted under 35 U.S.C. 154(b) by 169 days.

(21) Appl. No.: 13/582,124

(22) PCT Filed: Mar. 4, 2011

(86) PCT No.: PCT/IB2011/050926
§ 371 (c)(1),
(2), (4) Date: Aug. 31, 2012

(87) PCT Pub. No.: WO2011/110987
PCT Pub. Date: Sep. 15, 2011

(65) Prior Publication Data
US 2012/0321156 A1 Dec. 20, 2012

(30) Foreign Application Priority Data
Mar. 12, 2010 (EP) .................................. 10156297

(51) Int. Cl.
*G06K 9/00* (2006.01)
*G06T 7/20* (2006.01)
*H05G 1/64* (2006.01)

(52) U.S. Cl.
CPC ..... *G06T 7/2053* (2013.01); *G06T 2207/10121* (2013.01); *G06T 2207/30048* (2013.01); *G06T 2207/30101* (2013.01)

(58) Field of Classification Search
CPC .................................... G06T 1/00; G06K 9/00

USPC ......... 382/128, 129, 130, 131, 132, 133, 134; 378/4, 8, 21–27, 101, 901, 98.11, 378/98.12; 600/407, 410, 411, 425, 427
See application file for complete search history.

(56) References Cited

U.S. PATENT DOCUMENTS 7,545,967 B1 * 6/2009 Prince et al. ................... 382/130
8,428,220 B2 * 4/2013 Buijns et al. ............... 378/98.12
(Continued)

FOREIGN PATENT DOCUMENTS

JP           10031745 A      2/1998
JP     2006271484 A    10/2006
(Continued)

OTHER PUBLICATIONS

E. Oubel et al, "Analysis of Interacranial Aneurysm Wall Motion and Its Effects on Hemodynamic Patterns", Proceedings of the SPIE—the International Society for Optical Engineering SPIE—the International Society for Optical Engineering USA, vol. 6511, 2007.
(Continued)

*Primary Examiner* — Abolfazl Tabatabai (57) ABSTRACT

A method and an apparatus for motion visualization of a moving object in angiographic images are described. In a preferred embodiment of the method, first a mask image of the object of interest is acquired and a sequence of angiographic images of the object in different phases of motion of the object is acquired. Then, a first angiographic subtraction image and at least a second angiographic subtraction image are generated by subtracting the angiographic images from the mask image. Subsequently, a twice subtracted image is generated by subtracting the first angiographic subtraction image from the second angiographic subtraction image. In this way a double subtraction, i.e. a twice subtracted angiography is performed, to facilitate the assessment of the motion.

20 Claims, 4 Drawing Sheets

(56) References Cited

U.S. PATENT DOCUMENTS

| | | | |
|---|---|---|---|
| 8,498,463 B2 * | 7/2013 | Florent et al. | 382/130 |
| 2007/0104317 A1 * | 5/2007 | Ohishi | 378/98.12 |
| 2009/0067568 A1 * | 3/2009 | Hall et al. | 378/4 |

FOREIGN PATENT DOCUMENTS

| | | |
|---|---|---|
| JP | 2009297077 A | 12/2009 |
| WO | WO2008053401 | 5/2008 |

OTHER PUBLICATIONS

M. Sonka et al, "Image Processing, Analysis, and Machine Vision, Second Edition", Pacific Grove, Calif, Jan. 1, 1999, pp. 679-685.

Schad, "Nontraumatic Assessment of Left Ventricular Wall Motion and Regional Stroke Volume After Myocardial Infarction", Journal of Nuclear Medicine, Vol. 18, No. 4, 1977, pp. 333-341.

Anxionnat et al, "Intracranial Aneurysms: Clinical Value of 3D Digital Subtraction Angiography in the Therapeutic Decision and Endovascular Treatment", Radiology, Vol. 218, 2001, pp. 799-808.

Sonka et al, "Chapter 15 Motion Analysis, 15.1 Differential Motion Analysis Methods", Image Processing Analysis and Machine Vision, Jan. 1, 1999, pp. 679-685.

Cui, "Research on Moving Object Detection and Dtracking in Image Sequence", China Master'S Theses, No. 7, 2009, 79 Page Document.

Oubel et al, "Analysis of Intracranial Aneurysm Wall Motion and Its Effects on Hemodynamic Patterns", Proceedings of the SPIE, Vol. 6511, 2007, pp. 1-8.

* cited by examiner

MOTION VISUALISATION IN ANGIOGRAPHIC IMAGES

FIELD OF THE INVENTION

The invention relates to the visualization of motion in angiographic images. Particularly, the invention relates to a method and an apparatus for motion visualization of a moving object in angiographic images. Furthermore, the invention also relates to a computer program element enabling to control such method when executed on a computer and to a computer-readable medium on which such computer program element is stored.

BACKGROUND OF THE INVENTION

In many areas of science it may be important to supply images or image sequences of an object of interest to a viewer. In many applications the object of interest may be moving. Particularly, in some areas of medicine it may be important to provide accurate data about the motion of the object.

To provide good data and in particular good visualization of the moving object the images may be processed. For example a digital subtraction angiography as shown in JP 10 031 745 A may be performed.

However, an assessment of the motion from a sequence of images may be difficult, especially, if the motion is fast, irregular and/or small compared to the dimensions of the image or the motion of surrounding objects.

SUMMARY OF THE INVENTION

It would be advantageous to achieve an improvement in the visualization of the motion of an object of interest and thereby to enable a more reliable and accurate assessment of the motion.

According to a first aspect of the invention a method for motion visualization of a moving object of interest in angiographic images is provided. The method comprises the following steps: acquiring a mask image of the background of the object of interest and acquiring a sequence of angiographic images of the object in different phases of motion of the object; generating a first angiographic subtraction image and at least a second angiographic subtraction image by subtracting the angiographic images from the mask image; generating a twice subtracted image by subtracting the first angiographic subtraction image from the second angiographic subtraction image.

In other words, the first aspect of the invention may be seen as based on the idea to perform a double subtraction, i.e. a twice subtracted angiography, to facilitate the assessment of the motion. First, a digital subtraction angiography (DSA) is performed by subtracting a mask image from each of the acquired angiographic images or vice versa. The image sequence resulting from the DSA comprises at least two images, i.e. a first and at least a second angiographic subtraction image. The DSA provides angiographic subtraction images with an enhanced representation of the object of interest, e.g of vessel structures. After the DSA a second subtraction is performed in which one of the angiographic subtraction images generated in the DSA is subtracted from at least one further angiographic subtraction image generated in the DSA. I.e. e.g. a first angiographic subtraction image is subtracted from a second or from several second angiographic subtraction images. The second subtraction provides twice subtracted images showing only the difference between two angiographic subtraction images. Thus, only a displacement of the object in the images is visible. After the performing of the double subtraction the twice subtracted images may be presented to a viewer.

The acquiring of a sequence of angiographic images may denote retrieving from a database or memory or may denote an obtaining of images by a certain technique as for example x-ray imaging, particularly rotational X-ray imaging, computer tomography (CT), and magnetic resonance (MR). The images may be data, frames, sequences of frames, or visual representations thereof.

The moving object may also be denoted as object of interest. The moving object represented in the angiographic images may be a blood vessel, a heart, a coronary artery, an arterial venous malfunction and in particular an aneurysm.

The sequence of angiographic images comprises at least two and preferably several images acquired in a way such that the object of interest is visualized in an enhanced way such as e.g. after injection of a contrast medium. In the case of a periodic motion of the object the sequence of angiographic images may cover several cycles of motion. The sequence is for example a set or a series of images which follow each other in time and may be viewed for example as a movie.

The sequence of angiographic images represents the object in different phases of motion. The phases of motion may be related to a heart beat or to a respiration. In the case that the phase of motion depends on the heart beat angiographic images may represent for example a vessel or an aneurysm in different phases of the heart cycle like for example systole and diastole and phases between those two extreme phases. The moving object may move periodically i.e. pulsatile.

The mask image may be an image acquired during a time period in which no contrast agent is present in the object of interest such as the blood vessels. During the acquisition of the angiographic images contrast agent may be present in the blood vessels. The mask image and the angiographic images show the same object and region of interest, i.e. the mask image is an image of the same area before a contrast agent is present in the blood vessels. The angiographic images may be acquired during a time period in which contrast agent is present in the blood vessels. The mask image may be part of the sequence of the angiographic images and may be acquired before the acquisition of the angiographic images. The mask image may be subtracted from the angiographic images or alternatively the angiographic images may be subtracted from the mask image.

In the case of a periodic motion a mask image may be acquired for each phase of motion and subtracted from the corresponding angiographic images acquired at the same phase respectively.

The subtraction of the mask image from the sequence of angiographic images provides a first angiographic subtraction image and at least a second angiographic subtraction image in which for example the vessels are enhanced and distracting structures such as bones and dense tissue are removed. The mask image may be subtracted from each angiographic image of the sequence. In the second subtraction at least one twice subtracted image is generated by subtracting the angiographic subtraction images received in the first subtraction from each other. For example, a predeterminable image e.g. a fixed image i.e. the first angiographic subtraction image may represent the object of interest in the motion state corresponding to a systole. This first angiographic subtraction image may be subtracted from a second angiographic subtraction image representing a different phase of motion such as the diastole. The first angiographic subtraction image may be subtracted from all further angiographic subtraction images, i.e. second angiographic subtraction images, which are comprised in the sequence of angiographic images from which the mask image was already subtracted. The resulting twice subtracted image or images may only show the displacement of the object. This is particularly the case, when the surroundings of the object do not move compared to the object and are identical in the first and second angiographic subtraction images. Alternatively, a motion of the surrounding structures of the object may be negligibly small compared to the motion of the object. The first and the second subtraction may be performed simultaneously or preferably subsequently.

By generating twice subtracted images the detection and assessment of even small motions of small objects may be made possible and the assessment of this motion may be facilitated for a viewer.

According to an embodiment of the invention, the method comprises further averaging angiographic images representing the object in a same phase of motion.

In case of a periodically moving object the sequence of angiographic images may comprise several images representing the object in a same phase of motion if the sequence comprises several cycles of the motion. For example, in the case of a heart beat the sequence of angiographic images may comprise several heart beats and thus several angiographic images representing e.g. the systole and several representing the diastole. The images of the sequence of angiographic images may be first classified for example according to their heart phase and then images of the same phase may be averaged. Thus, for example a sequence of angiographic images which represents several heart cycles after the averaging step represents only one heart cycle.

The averaging may enhance the quality and accuracy of the generated images by reducing noise and furthermore by for example reducing irregularities in the contrast agent concentration present in the blood vessels.

According to a second aspect of the invention an apparatus for motion visualization of a moving object in angiographic images is provided. The apparatus comprises a first subtractor for generating a first angiographic subtraction image and at least a second angiographic subtraction image by subtracting angiographic images from a mask image. The apparatus further comprises a second subtractor for generating a twice subtracted image by subtracting the first angiographic subtraction image from the second angiographic subtraction image.

The apparatus may further comprise an image detector or image retriever for acquiring images of an object in different phases of motion. Furthermore the apparatus may comprise for example a display or a screen for providing the result of the second subtraction, i.e. the twice subtracted image such that the difference due to the motion of the object is visualizable. The first and the second subtractor may be units of the apparatus which are connected to each other and/or to a memory and a processor.

According to a third aspect of the invention a computer program element enabling to control the method described above when executed on a computer is presented.

According to a fourth aspect of the invention a computer-readable medium with a computer program element described above is presented.

It has to be noted that embodiments of the invention are described with reference to different subject-matters. In particular, some embodiments are described with reference to method type claims whereas other embodiments are described with reference to apparatus type claims. However, a person skilled in the art will gather from the above and the following description that, unless other notified, in addition to any combination of features belonging to one type of subject-matter also any combination between features relating to the different subject-matters, in particular between features of the apparatus type claims and features of the method type claims, is considered to be disclosed with this application.

The aspects defined above and further aspects, features and advantages of the present invention can be derived from the examples of embodiments described hereinafter. The invention will be described in more detail hereinafter with reference to examples of embodiments but to which the invention is not limited.

DETAILED DESCRIPTION OF EMBODIMENTS

In the following examples of embodiments the object which is subjected to a motion may be an aneurysm. Before a treatment of an aneurysm is possible it should be assessed whether the risk of rupture is higher during the treatment or if the aneurysm should be left untreated. Aneurysm wall motion might be one factor indicative for the risk of rupture. The aneurysm wall motion is related to local biomechanical properties of the aneurysm which in turn are associated with the amount of damage undergone by the tissue. If one part of the aneurysm wall moves more than another part there might be a weak spot in the wall which could increase the risk of rupture. In the case that the aneurysm wall does not move this could indicate a low risk of rupture. Therefore, it may be important to visualize the motion of an aneurism wall to assess the situation.

Aneurysms may be visualized with the help of angiographic images. The assessment of the aneurysm wall motion from a sequence of angiographic images may be difficult. For example, the sequence of angiographic images may be acquired at a rate of 5 frames or images per second. Preferably, the angiographic sequence is acquired at a high rate of about 30 frames or images per second. If such a sequence is played with normal speed the motion is visible as a flicker but is nevertheless difficult to assess. If the sequence is played with a very low speed the motion is no longer visible because it is too small. Moreover, methods which require the selections of frames from the sequence to enhance the quality of the representation require a user interaction and are therefore not precise and very time-consuming.

Figure 1:
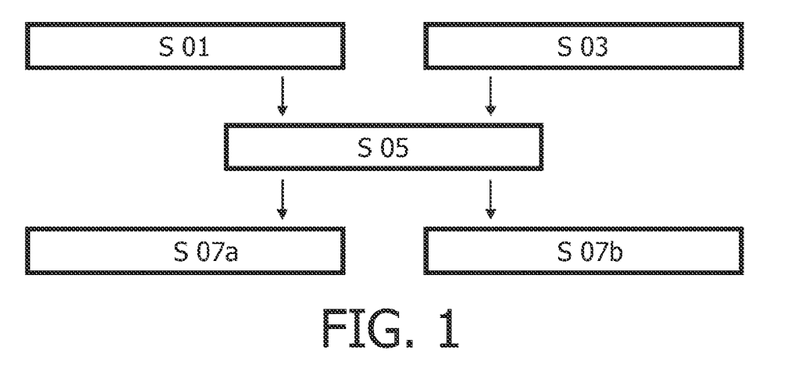
FIG. 1 shows a flow diagram schematically representing a method for motion visualization according to an embodiment of the invention
Figure 2:
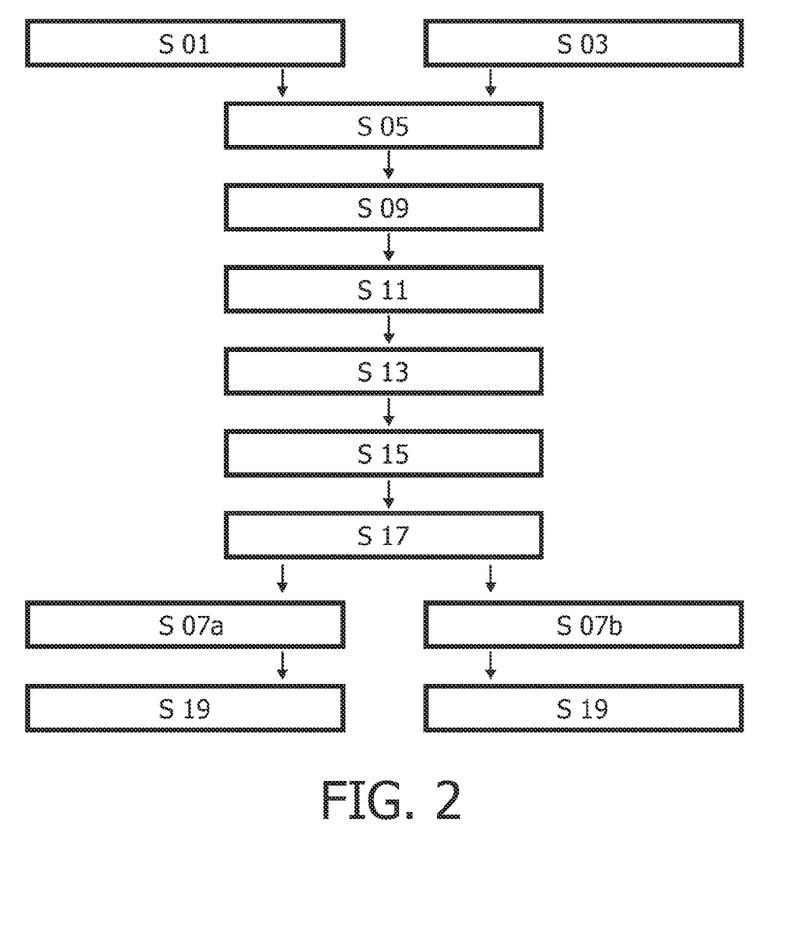
FIG. 2 shows a flow diagram schematically representing a method for motion visualization according to a further embodiment of the invention FIG. 3A schematically shows averaged angiographic subtraction images representing an aneurism in different phases of the cardiac cycle to be used in an embodiment of the invention FIG. 3B schematically shows twice subtracted images of the aneurism in FIG. 3A generated according to an embodiment of the invention

The embodiments of the method shown in FIG. 1 and FIG. 2 may help to provide a better motion visualization and thus to facilitate the assessment of e.g. the aneurysm wall motion.

FIG. 1 shows a flow diagram schematically representing a method for motion visualization according to an embodiment of the invention. In step S1 a mask image of the object e.g. an aneurysm is acquired. In step S3 a sequence of angiographic images of the object in different phases of motion of the object is acquired. The acquisition of the mask image takes place before a contrast agent is present in the object. The sequence of angiographic images is acquired during a contrast agent is present in the object. The acquiring of the mask image may also be part of step S3. Alternatively step S1 and step S3 may be executed simultaneously or subsequently. In a simultaneous execution of step S1 and S3 the mask image may be retrieved from a data bank during the acquisition of the sequence of angiographic images.

In step S5 a first subtraction is performed. Therein, a first angiographic subtraction image and at least a second angiographic subtraction image are generated by subtracting the angiographic images from the mask image or by subtracting the mask image from the angiographic images. The first angiographic subtraction image and the second angiographic subtraction image represent different phases of motion of the object. Moreover, the phase of motion may represent a phase of periodical motion of the object.

The phase of motion may for example be a heart phase such as a systole or a diastole. Moreover, the phase of motion may for example be a respiration phase such as an inhalation or an exhalation. Furthermore, the phase of motion may be a superposition of several motions such as a combination of a heart beat and a respiration motion.

In step S7a and S7b a second subtraction is performed. In step S7a a twice subtracted image is generated by subtracting the first angiographic subtraction image from the second angiographic subtraction image. Alternatively in step S7b several twice subtracted images are generated by subtracting the first angiographic subtraction image from several preferably all second angiographic subtraction images. For example, according to step S7a the twice subtracted image may represent the difference of a systolic and a diastolic motion phase. According to step S7b the second subtraction may result in a sequence of twice subtracted images: one predefineable image, e.g. a fixed image, namely the first angiographic subtraction image representing one heart phase is subtracted from the other angiographic subtraction images namely the second angiographic subtraction images.

The steps of the method may be executed automatically. Automatically may denote without the necessity of a user interaction. Automaticity of the method may provide qualitatively better and more accurate data which may be better reproducible than data generated with methods which need user interaction.

The moving object may be an aneurysm, a vessel structure, a heart or a vessel malformation. Furthermore the motion may be caused by a heart beat and be represented by a phase of a heart cycle and/or it may be caused by a respiration and be represented by a phase of a respiration cycle.

In FIG. 2 a flow diagram schematically representing a method for motion visualization according to a further embodiment of the invention is presented.

Steps S1, S3, S5, S7a and S7b are performed in analogy to the examples shown in FIG. 1. After the first subtraction in step S5 some further steps S9 to S17 may be included in the method. Moreover, step S19 may follow steps S7a and/or S7b.

After the angiographic subtraction images of the DSA are generated in step S5 angiographic subtraction images in which the object i.e. the aneurysm is filled with contrast agent may be selected (step S9). Alternatively, images of the sequence of angiographic images are selected in which contrast agent is present in the vessels before the first subtraction is preformed in step S5. I.e. step S9 may be executed after step S3. Step S9 may enhance the quality of the resulting twice subtracted images because for example noise may be reduced by sorting out images without contrast agent.

In step S11 the phase of motion in at least two angiographic subtraction images received after the DSA is determined. Preferably, the phase of motion in all the angiographic subtraction images is determined. For example, in step S11 the angiographic subtraction images may be classified according to their heart phase. The classification may be electrocardiogram-based (ECG-based) or image-based. For the determination of the phase of motion a motion signal representative of the motion, as for example an ECG signal or a respiration signal, are acquired. The ECG signal may allow for a precise determination of the phase of motion and thus, enable a precise classification of the angiographic subtraction images. The ECG-signal may be acquired in parallel to steps S1 and S3 or may alternatively be retrieved from a database. The acquisition of an ECG-signal in parallel to step S1 may allow for a classification of several mask images such that for example a mask image acquired in the phase of systole may be subtracted from the corresponding angiographic subtraction images acquired in the phase of systole. Thereby, the image quality may be further enhanced.

Alternatively, the determination of the phase of motion in the angiographic subtraction images is based on an analysis of the angiographic subtraction images themselves. An image-based classification may require a less complicated apparatus.

Step S11 may alternatively be executed after step S3 and before step S5. I.e. the classification may be based on the sequence of angiographic images before the DSA in step S5. Furthermore, the determination of the phase of motion may be based on an analysis of the angiographic images before the DSA in step S5.

After the determination of the phase of motion in step S11 a first angiographic subtraction image is selected in step S13. The first angiographic subtraction image may be selected such that the phase of motion represented in the first angiographic subtraction image is an extreme phase of motion. An extreme phase of motion may be a phase of motion which results in the most or in the least deformation of the object. In the case of a heart cycle the extreme phases of motion may be the systole and the diastole. The selection of the first angiographic subtraction image representing a phase of motion which is extreme may help in enhancing the quality of the motion visualization because in an extreme phase of motion the deformation of the object may be greatest compared to the other angiographic images of the sequence.

Furthermore, in step S15 the angiographic images may be registered rigidly after step 03. I.e. a spatial correspondence between at least two angiographic images is determined. In other words the images are aligned by changing one of the images by rotating and translating it. Alternatively, the registration step S15 may be implemented with the angiographic subtraction images after step S5. I.e. after the first subtraction in step S5 the first and second angiographic subtraction images may be registered.

In the case of an aneurysm as the moving object of interest two different types of pulsatile motion are known. A pulsatile extension and a pulsatile rocking of the aneurysm and also of the parent artery are possible. Both types of motion can be enhanced in the visualization according to this embodiment. In the case that only a pulsatile extension is to be visualized the angiographic images representing the different phases of motion may be registered to each other with a rigid registration before the subtraction in step S7a and 7b. Therein, in a rigid registration two images may be aligned by compensating a translation and a rotation of the images in relation to each other. A rigid registration may be advantageous because it does not remove the motion to be visualised from the images due to the avoiding of a deformation of the images during registration.

In step S17 an averaging of angiographic subtraction images representing the object in the same phase of motion is performed. The averaging in step S17 may be based on the determination of the phase of motion performed in step S11. For example, the images of the same heart phase are averaged in order to reduce the influence of variations in the contrast agent concentration and to reduce noise. Thus, in step S17 an averaged sequence of angiographic subtraction images is generated which represents one heart cycle. Examples of an averaged sequence of angiographic subtraction images of an aneurysm in different phases of a cardiac cycle are shown in FIGS. 3A, 4A and 5A and denoted with the reference sign 3.

Alternatively, the averaging step S17 may be executed before the first subtraction in step S11. I.e. the angiographic images may be averaged.

After the averaging step S17, step S7a or step S7b is executed. Therein, a first angiographic subtraction image which may be the averaging result of angiographic subtraction images representing the same phase of motion is subtracted from a second angiographic subtraction image which may be the averaging result of angiographic subtraction images of a different phase of motion (step S7a). Alternatively, in step S7b the first angiographic subtraction image which is an averaging result is subtracted from each second angiographic subtraction image wherein the second angiographic subtraction images represent averaging results from the other phases of motion.

In other words, the first angiographic subtraction image is a selected, e.g. fixed image, for example representing the end diastolic phase. This fixed image is subtracted from the averaged sequence of angiographic subtraction images. The result of this subtraction is the twice subtracted angiographic image sequence.

Alternatively, the selecting step of the first angiographic subtraction image representing an extreme phase of motion in step S13 may be performed after the averaging step S17 and before step S7a or 7b. Examples of a sequence of twice subtracted images of the aneurysm are shown in FIGS. 3B, 4B and 5B and denoted with the reference sign 5.

In step S19 twice subtracted images are displayed. It is possible to provide i.e. display the result of the first subtraction, the averaging result and the result of the second subtraction for example immediately after the respective step is executed or alternatively after all steps are executed. The mentioned results may be visualized on different displays or alternatively on the same display. Furthermore, they may be visualized subsequently or at the same time.

Figure 3:
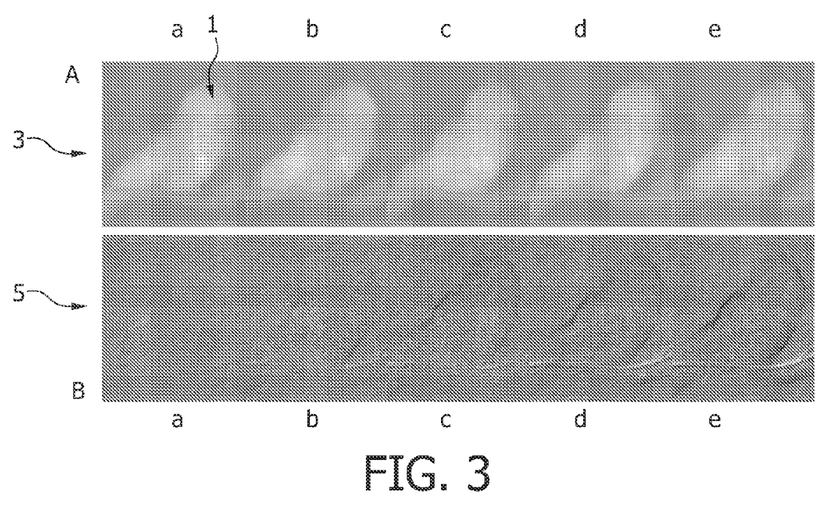
Figure 4:
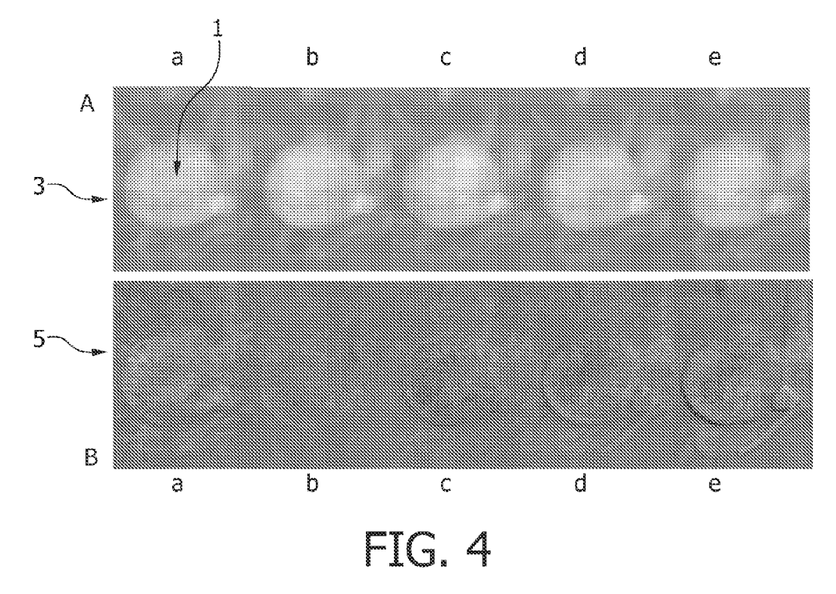
FIGS. 4A and 4B show a further example of image sequences in analogy to FIGS. 3A and 3B FIGS. 5A and 5B show a further example of image sequences in analogy to FIGS. 3A and 3B FIG. 6 schematically shows an apparatus for motion visualization of a moving object in angiographic images according to an embodiment of the invention The illustration in the drawings is schematic only. It is noted that in different figures, similar or identical elements are provided with the same reference signs.
Figure 5:
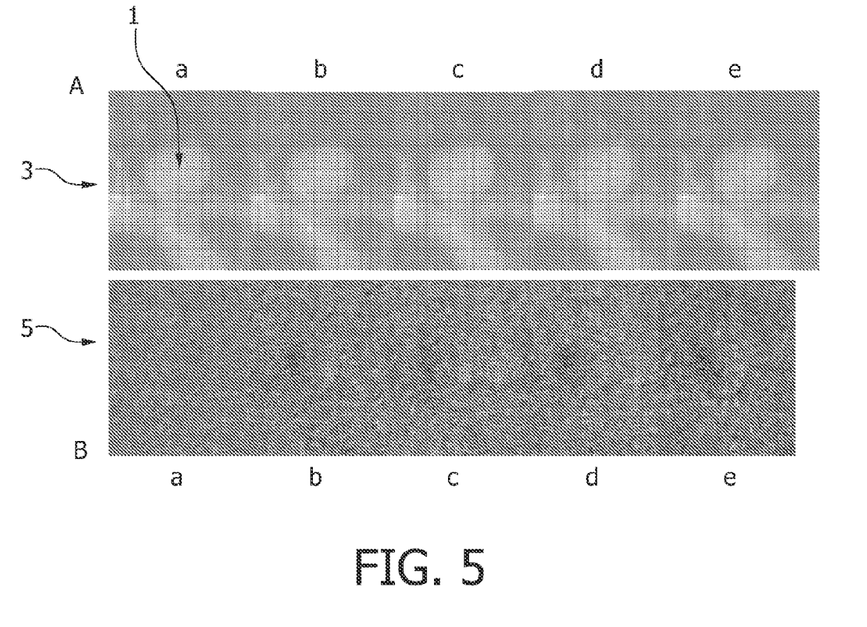

In FIGS. 3, 4 and 5 examples of a visualization of angiographic sequences are shown. Therein, in FIGS. 3A, 4A and 5A averaged angiographic images are represented after a first subtraction (step S5) and an averaging (step S17) are performed.

In FIGS. 3B, 4B and 5B the visualization of a sequence of twice subtracted images after the performing of step S7b is presented. Object 1 which here is an aneurysm is shown in different phases of motion (a, b, c, d, e). In the averaged DSA sequence shown in FIGS. 3A, 4A and 5A no wall motion of the aneurysm is visible. After the second subtraction the aneurysm wall motion becomes visible in FIGS. 3B and 4B. The aneurysm shown in FIG. 5 shows no motion as may be seen from the presentation in FIG. 5B. The lack of motion of the object is the reason for the "blank" presentation after the second subtraction in FIG. 5B.

In the example in FIG. 3A an angiographic subtraction image representing the end diastolic phase (a) is subtracted from the second angiographic subtraction images representing the motion phases b, c, d and e. As shown in FIG. 3B the first image shows a "blank" presentation because the first angiographic subtraction image is subtracted from itself in this representation. The most difference is visible when the first angiographic subtraction image is subtracted from the second angiographic subtraction image in the systolic phase (e).

Figure 6:
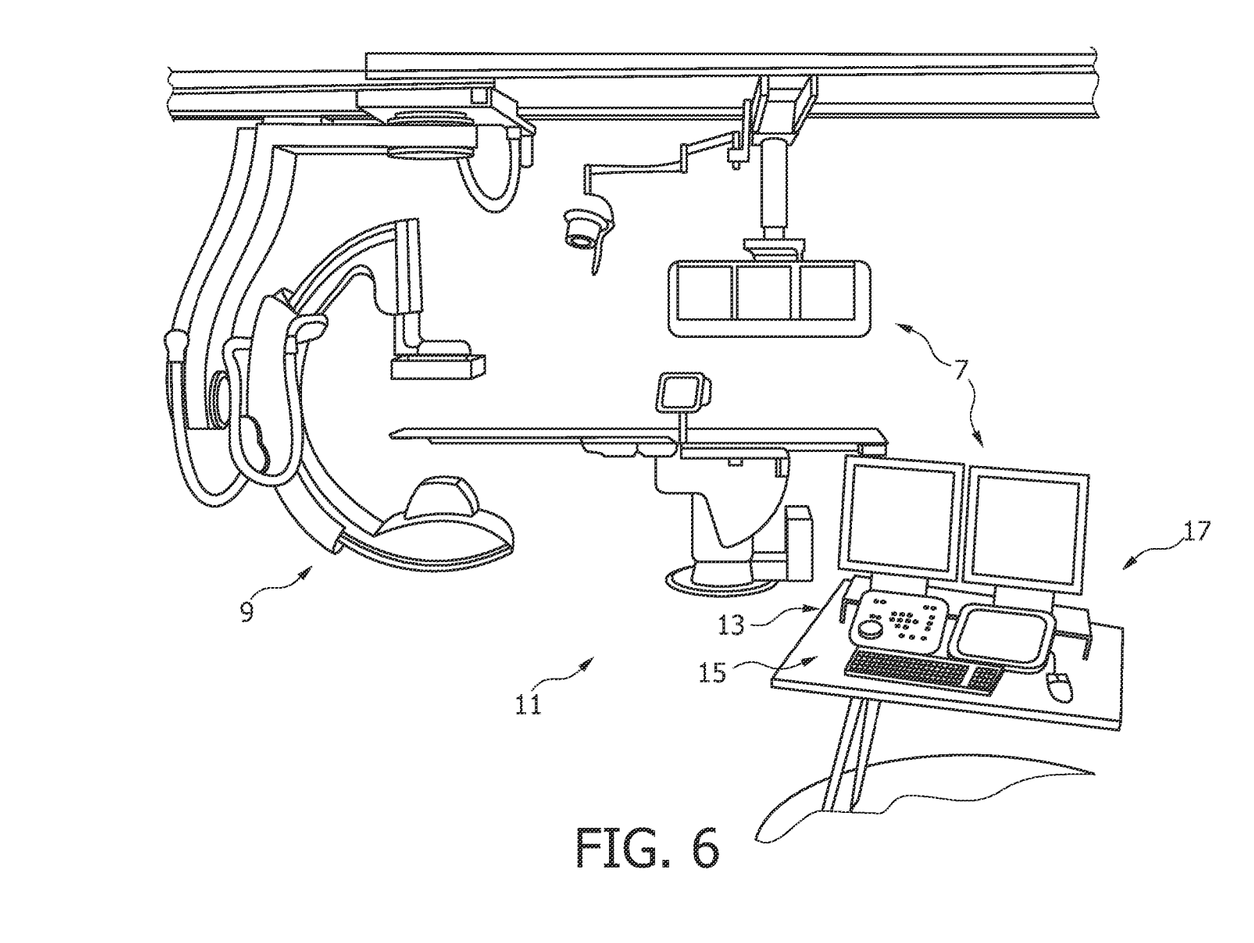

In FIG. 6 an apparatus 11 for motion visualization of a moving object in angiographic images is shown schematically according to an embodiment of the invention.

The apparatus 11 comprises a C-arm with an X-ray detector 9 and a data storing device which may both serve for acquiring a sequence of angiographic images of the object. Therein, the data storing device may be incorporated in the processor 17. The apparatus 11 further comprises a first subtractor 13 for generating a first angiographic subtraction image and at least a second angiographic subtraction image by subtracting angiographic images from a mask image.

Furthermore, the apparatus 11 comprises a second subtractor 15 for generating a twice subtracted image by subtracting the first angiographic subtraction image from the second angiographic subtraction image. The first subtractor 13 and the second subtractor 15 may be part of or may be connected to the processor 17. Moreover, the apparatus 11 may comprise one or several displays 7 for providing the result of the second subtraction such that the difference in the motion of the object is visualizable. The processor 17, the display 7 and the X-ray detector 9 may be connected by cable or wirelessly.

It should be noted that the terms "comprising", "including" etc. do not exclude other elements or steps and the "a" or "an" does not exclude a plurality. Also elements described in association with different embodiments may be combined. It should also be noted that reference signs in the claims should not be construed as limiting the scope of the claims. Furthermore, a computer program may be stored and/or distributed on a suitable medium, such as an optical storage medium or a solid state-medium supplied together with or as part of other hardware, but may also be distributed in other forms such as via the Internet or other wired or wireless telecommunication systems.

LIST OF REFERENCE SIGNS 1 object
3 sequence of averaged angiographic images representing an aneurism in different phases of a cardiac cycle
5 sequence of twice subtracted images of the aneurism
7 display
9 x-ray detector
11 apparatus for motion visualization
13 first subtractor
15 second subtractor
17 processor a-e different phases of motion
S1 acquiring a mask image of the object
S3 acquiring a sequence of angiographic images of the object in different phases of motion of the object
S5 generating a first angiographic subtraction image and at least a second angiographic subtraction image by subtracting the angiographic images from the mask image
S7a generating a twice subtracted image by subtracting the first angiographic subtraction images from the second angiographic subtraction image
S7b generating several twice subtracted image by subtracting the first angiographic subtraction image from several second angiographic subtraction images
S9 selecting angiographic images in which the object is filled with contrast agent
S11 determining the phase of motion in at least two angiographic images
S13 selecting the first angiographic subtraction image such that the phase of motion represented in the first angiographic subtraction image is an extreme phase of motion
S15 registering the angiographic images
S17 averaging angiographic images representing the object in the same phase of motion
S19 displaying the twice subtracted images

The invention claimed is:

1. A method for motion visualization of a moving object in angiographic images, the method comprising:
   acquiring a sequence of angiographic images of the object in different phases of motion of the object and a mask image of the object;
   generating a first angiographic subtraction image and at least a second angiographic subtraction image by subtracting the angiographic images from the mask image; and
   generating a twice subtracted image by subtracting the first angiographic subtraction image from the second angiographic subtraction image.

2. The method according to claim 1, further comprising averaging angiographic subtraction images representing the object in the same phase of motion.

3. The method according to claim 1, further comprising the step of selecting the first angiographic subtraction image such that the phase of motion represented in the first angiographic subtraction image is an extreme phase of motion.

4. The method according to claim 1, wherein the first angiographic subtraction image and the second angiographic subtraction image represent different phases of motion of the object.

5. The method according to claim 1, wherein the phase of motion represents a phase of a periodical motion of the object.

6. The method according to claim 1, further comprising determining the phase of motion in at least two angiographic subtraction images.

7. The method according to claim 6, further comprising acquiring a motion signal representative of the phase of motion of the object; wherein the determination of the phase of motion in the angiographic subtraction images is based on the motion signal.

8. The method according to claim 6, wherein determination of the phase of motion in the angiographic subtraction images is based on an analysis of the subtraction angiographic images.

9. The method according to claim 1, further comprising selecting angiographic subtraction images in which contrast agent is present in the object.

10. The method according to claim 1, wherein the steps of the method are executed automatically.

11. The method according to claim 1, further comprising determining a spatial correspondence between at least two of the angiographic images.

12. The method according to claim 1, wherein the moving object is one of an aneurism, a vessel structure, a vessel malformation and a heart; wherein the phase of motion represent the phase of a heart cycle and/or a phase of a respiration cycle.

13. An apparatus, for motion visualization of a moving object in angiographic images, the apparatus comprising:
   a first subtractor for generating a first angiographic subtraction image and at least a second angiographic subtraction image by subtracting angiographic images from a mask image; and
   a second subtractor for generating a twice subtracted image by subtracting the first angiographic subtraction image from the second angiographic subtraction image.

14. The apparatus of claim 13, configured for averaging angiographic subtraction images representing the object in the same phase of motion.

15. The apparatus of claim 13, the first and second subtractors being configured for performing their respective generating, from the corresponding images, automatically, without need for user interaction.

16. The apparatus of claim 13, said angiographic images being of the object in different phases of motion of the object, said apparatus being configured for selecting the first angiographic subtraction image such that the phase of motion represented in the first angiographic subtraction image is an extreme phase of motion.

17. The apparatus of claim 13, the first angiographic subtraction image and the second angiographic subtraction image representing different phases of motion of the object.

18. The apparatus of claim 13, said angiographic images being of the object in different phases of motion of the object, the phase of motion representing a phase of a cyclical motion of the object.

19. The apparatus of claim 13, configured for determining, from among said first angiographic subtraction image and at least a second angiographic subtraction image, the phase of motion in at least two angiographic subtraction images.

20. A computer readable medium embodying a computer program for motion visualization of a moving object in angiographic images, said program having instructions executable by a processor for performing a plurality of acts, among said plurality there being the acts of:
   acquiring a sequence of angiographic images of the object in different phases of motion of the object and a mask image of the object;
   generating a first angiographic subtraction image and at least a second angiographic subtraction image by subtracting the angiographic images from the mask image; and
   generating a twice subtracted image by subtracting the first angiographic subtraction image from the second angiographic subtraction image.

* * * * *